United States Patent [19]

Hudson

[11] 4,350,158

[45] Sep. 21, 1982

[54] PULSATING SPRAY NOZZLE

[76] Inventor: Raymond A. Hudson, 7415 Universal, Houston, Tex. 77072

[21] Appl. No.: 118,541

[22] Filed: Feb. 4, 1980

[51] Int. Cl.³ ............................................. A61M 3/00
[52] U.S. Cl. .................................... 128/224; 128/230; 128/239; 239/383; 239/460; 308/9; 222/386.5
[58] Field of Search ..................... 128/66, 200.14, 239, 128/230, 224, 225; 137/624.14; 239/381, 383, 460, 283; 308/9; 222/386.5

[56] References Cited

U.S. PATENT DOCUMENTS

| | | | |
|---|---|---|---|
| 2,570,682 | 10/1951 | Imbert .................................... | 308/9 |
| 2,688,515 | 9/1954 | Filliung ................................ | 239/460 |
| 3,637,143 | 1/1972 | Shames et al. ........................ | 239/283 |
| 4,081,135 | 3/1978 | Tomaro ................................. | 239/102 |
| 4,101,075 | 7/1978 | Heitzman ............................. | 239/383 |
| 4,203,550 | 5/1980 | On ......................................... | 239/383 |

FOREIGN PATENT DOCUMENTS

| | | | |
|---|---|---|---|
| 1027364 | 4/1958 | Fed. Rep. of Germany ........ | 128/66 |
| 658036 | 5/1929 | France ............................. | 128/200.14 |

*Primary Examiner*—Henry J. Recla
*Attorney, Agent, or Firm*—Neal J. Mosely

[57] ABSTRACT

A pulsating spray nozzle is particularly useful in an irrigation lavage for medical or veterinary use in delivering pulsating streams of liquid for cleansing wounds. The spray nozzle is designed to provide a steady operation over a wide range of flow rates. The nozzle comprises a hollow portable housing having an inlet connectable to a source of fluid. The nozzle housing has an end closure member providing an end wall having a plurality of fluid discharge orifices located symmetrically around the longitudinal axis of the housing. A rotary valve member is positioned in the housing for rotation along the surface of the end wall to control flow of liquid through the orifices therein. The rotary valve member comprises an arcuate valve plate supported on and integral with a plurality of radially extending vanes. The valve plate is curved or arcuate in cross-section and has a plurality or radial grooves in the face thereof to permit flow of liquid along said face to permit steady rotation thereof throughout a wide range of flow rates. A removable wall member is positioned in the housing securing said valve member in place and having a plurality of angularly directed holes for directing liquid flow against said vanes to rotate said valve member to effect a pulsating flow of liquid through said orifices. A flow control valve is positioned in the inlet end of said housing and actuated by a handle supported thereon.

9 Claims, 7 Drawing Figures

4,350,158

PULSATING SPRAY NOZZLE

BACKGROUND OF THE INVENTION

1. Field of the Invention

This invention relates to new and useful improvements in pulsating spray nozzles and particularly in pulsating spray nozzles useful in an irrigation lavage for medical or veterinary use.

2. Brief Description of the Prior Art

Mullins U.S. Pat. No. 3,912,168 discloses an irrigation lavage having a special pump arrangement for delivering a pulsating flow of liquid for use in medical or similar applications.

Simmons U.S. Pat. No. 1,473,979 discloses an apparatus for supplying liquids from a collapsible container by application of fluid pressure to collapse the supply container.

Erwin U.S. Pat. No. 2,878,066 discloses a showerhead having a rotary valve for providing a pulsating flow.

Trupp U.S. Pat. No. 3,690,314 discloses an attachment for a faucet whereby water is caused to pulsate as it is discharged for application in a dental appliance.

Deines U.S. Pat. No. 3,762,648 discloses a showerhead having a spray nozzle with a rotary valve for providing a pulsating flow of liquid.

Bauer U.S. Pat. No. 3,770,200 discloses a hand-held showerhead having a valve arrangement for providing a pulsating flow.

Trenary U.S. Pat. No. 3,801,019 discloses a spray nozzle or showerhead which is operable to discharge a continuous spray or a pulsating spray of adjustable frequency.

Tomaro U.S. Pat. No. 4,081,135 discloses a showerhead which is capable of producing a pulsating or a steady spray and includes a rotary valve operated by flow of liquid through the showerhead.

SUMMARY OF THE INVENTION

One of the objects of this invention is to provide a new and improved pulsating spray nozzle of general application and particularly adapted for use as part of a medical or veterinary irrigation lavage.

Another object of this invention is to provide a new and improved pulsating spray nozzle characterized by steady operation throughout a wide range of liquid flow rates.

Still another object of this invention is to provide a new and improved pulsating spray nozzle having a rotary valve member for producing a pulsating stream of liquid and said valve member having a surface configuration permitting fluid flow in a manner effecting a steady rotation thereof throughout a wide range of flow rates.

Other objects of this invention will become apparent from time to time throughout the specification and the claims as hereinafter related.

The pulsating spray nozzle of this invention meets the above stated objectives and is particularly useful in an irrigation lavage for medical or veterinary use in delivering pulsating streams of liquid for cleansing wounds. The spray nozzle is designed to provide a steady operation over a wide range of flow rates. The nozzle comprises a hollow portable housing having an inlet connectable to a source of fluid. The nozzle housing has an end closure member providing an end wall having a plurality of fluid discharge orifices located symmetrically around the longitudinal axis of the housing. A rotary valve member is positioned in the housing for rotation along the surface of the end wall to control flow of liquid through the orifices therein. The rotary valve member comprises an arcuate valve plate supported on and integral with a plurality of radially extending vanes. The valve plate is curved or arcuate in cross-section and has a plurality of radial grooves in the face thereof to permit flow of liquid along said face to permit steady rotation thereof throughout a wide range of flow rates. A removable wall member is positioned in the housing securing said valve member in place and having a plurality of angularly directed holes for directing liquid flow against said vanes to rotate said valve member to effect a pulsating flow of liquid through said orifices. A flow control valve is positioned in the inlet end of said housing and actuated by a handle supported thereon.

DESCRIPTION OF THE PREFERRED EMBODIMENT

Figure 1:
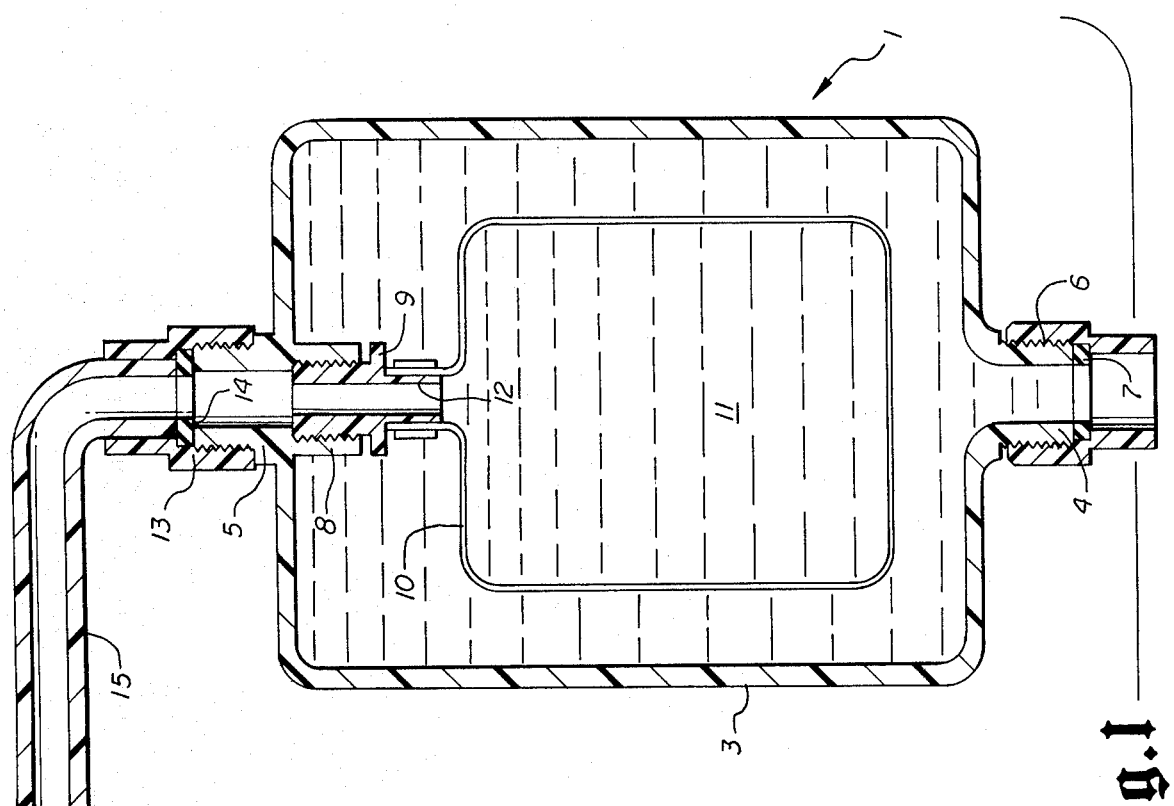
FIG. 1 is a view in longitudinal section, and partially exploded, showing a new and improved medical or veterinary irrigation lavage and novel pulsating spray nozzle therefor.
Figure 1:
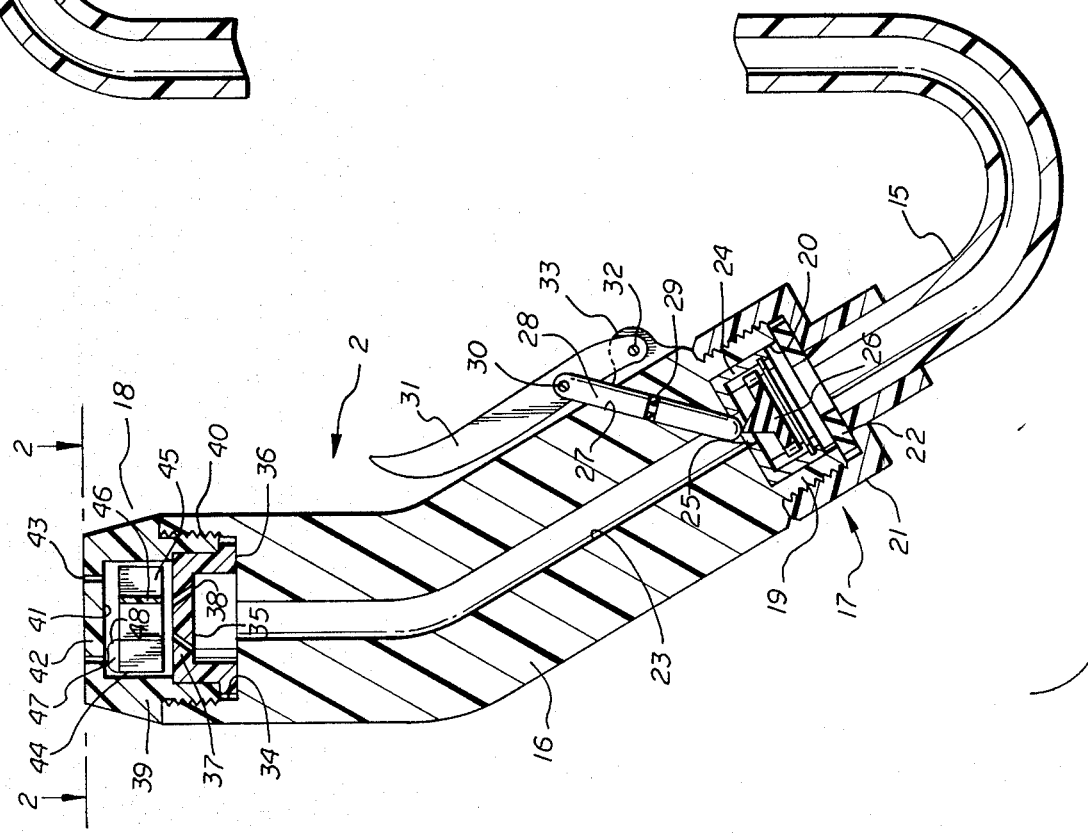
Figure 2:
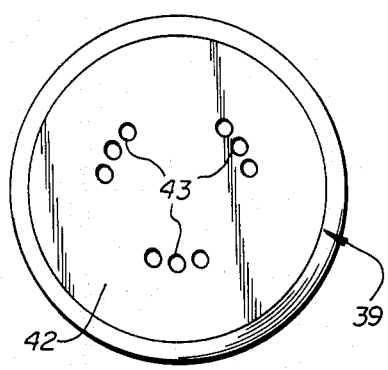
FIG. 2 is an end view of the spray nozzle as viewed on the line 2—2 of FIG. 1.
Figure 3:
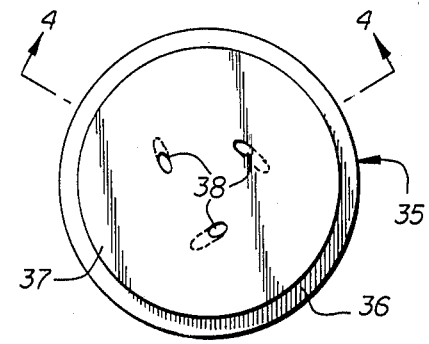
FIG. 3 is a top view of a valve retaining member in the spray nozzle of FIG. 1.
Figure 4:
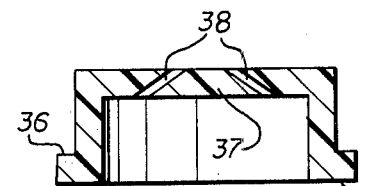
FIG. 4 is a sectional view of the valve retaining member taken on the line 4—4 of FIG. 3.
Figure 7:
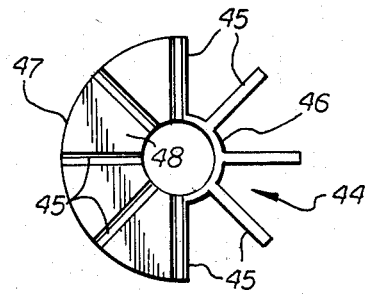
FIG. 7 is a bottom plan view of the rotary valve member shown in FIG. 1.
Figure 5:
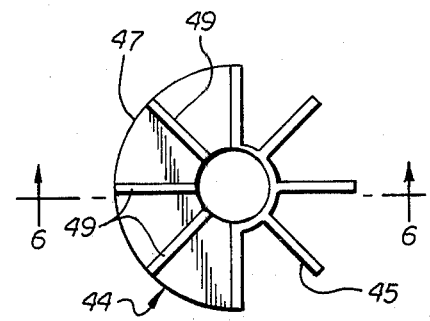
FIG. 5 is a top plan view of a rotary valve member from the spray nozzle shown in FIG. 1.

Referring to the drawings by numerals of reference and more particularly to FIG. 1, there is shown a pulsating medical/veterinary lavage comprising spray tank 1 and pulsating spray nozzle 2. Pulsating spray nozzle 2 is particularly designed for use as part of a lavage but is of a general application and could be used to provide a pulsating spray to a showerhead or other cleansing unit.

Supply tank 1 consists of housing 3 having inlet 4 and outlet 5. Inlet 4 is adapted to be connected by suitable threaded fitting 6 and washer 7 to an external source of liquid or gas under pressure. Housing 3 is provided with a threaded inwardly projecting abutment 8 which is part of outlet 5. Abutment 8 has a threaded plug 9 secured therein and has a thin walled flexible container 10 secured thereon. Flexible container 10 is adapted to supply a medical or veterinary cleansing liquid 11 by application of fluid pressure to the exterior of container 10 to cause the same to collapse. The threaded abutment member 9 has outlet passage 12 open to outlet 5 for discharge of cleansing liquid 11 therefrom. Outlet member 5 has a coupling 13 and washer 14 secured thereon sealing one end of fluid conduit 15. The other end of fluid conduit 15 is connected to the inlet end of pulsating spray nozzle 2.

Pulsating spray nozzle 2 comprises a hollow housing 16 which is preferably of size and shape suitable for manual operation. Housing 16 has a fluid inlet end 17 and a fluid outlet end 18. Fluid inlet end comprises threaded end portion 19 having an enlarged opening 20 therein. Threaded end portion 19 has coupling number 21 secured thereon and washer 22 securing in place the other end of fluid conduit 15.

Housing 16 is provided with longitudinally extending passage 23 which extends from enlarged chamber portion 20 to the outlet end of spray nozzle 2. Enlarged chamber portion 20 has valve retaining cup 24 secured therein which has an opening 25 providing a valve seat for valve member 26. Valve member 26 is normally secured in a closed position by application of fluid pressure through conduit 15. Housing 16 has a passage 27 in which there is positioned a valve actuating rod 28 which is secured against leakage by an O-ring seal 29. Rod 28 is secured by a pin connection 30 to a movable handle 31 which is pivotally connected as at 32 on a pivot hinge 33. In FIG. 1, handle 31 is shown in a position moved to a point where valve member 26 is held open to permit flow of liquid through the device.

At the outlet end 18 of spray nozzle 2, housing 16 has an enlarged counterbore providing a chamber 34. A removable cup shaped member 35 is positioned in chamber 34 and has a peripheral flange 36, by which it is held in position. The end wall 37 of cup shaped member 35 is provided with a plurality of passageways or orifices 38. Orifices 38 are preferably spaced 120° apart and extends through end wall 37 at a relatively low angle, preferably about 35°, relative to the end wall. The angle of orifices 38 is such that liquid passing through the orifices emerges as three distinct jets.

At the end of cavity 34 is closed by cup shaped closure member 39 which is secured by threaded connection 40. Closure member 39 has an interior cavity 41 which lies between end wall 37 of cup shaped number 35 and end wall 42 of cup shaped closure member 39. End wall 42 of closure member 39 is provided with a plurality of outlet passages over orifices 43 which are preferably arranged in groups of three and spaced 120° part around the longitudinal axis.

Figure 6:
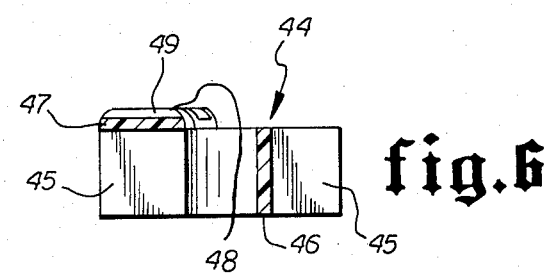
FIG. 6 is a sectional view taken on the line 6—6 of FIG. 5.

A rotary turbine or valve member 44 is positioned in chamber 41 and rotates along the inner surface of wall 42 to control discharge of liquid through orifices 43. Rotary valve member 44 consists of a plurality of radially extending vanes 45 which are secured together along one side on a half sleeve or half cylindrical portion 46 and, on the other side, are secured together along the top by valve plate 47. Valve member 44 has a longitudinal central opening 48 as seen in the various detail views thereof. Valve plate member 47 is preferably arcuate in shape, as shown, and has a curved or arcuate surface 48 which is traversed by three radially extending grooves 49. The curvature of the face 48 in longitudinal section (see FIG. 6) of valve plate member 47 and the provision of radial grooves 49 provides for fluid along the face of valve plate 47 during operation which functions to support the same a short predetermined distance from the end wall 42 of cup shape enclosure 39 so that valve member 44 can rotate in a steady manner throughout a wide range of rates of fluid flow through the flow nozzle.

OPERATION

The operation of this apparatus should be apparent from the foregoing description of the component parts and the manner of assembly thereof. However, a more thorough description of operation will be given to permit a more complete understanding of the apparatus.

This pulsating medical/veterinary lavage was designed to pulse a concentrated jet of liquid into a wound to cleanse and dislodge foreign debris and to flush the material out that could lead to irritation of the wound and retard healing. The force and speed of the jet of liquid is controlled by valve 26 and handle 31 mounted in the handle portion of spray nozzle housing 16.

The cleansing liquid 11 is provided in flexible, collapsable container 10 which is positioned inside liquid housing 3. The application of fluid pressure, either liquid or gasses pressure, through inlet 4 will cause container 10 to collapse and eject fluid 11 through outlet passage 12 and outlet 5, through conduit 15 to pulsating spray nozzle. 2.

The actuation of handle 31 is effective to cause push rod 27 to move valve member 26 to an open position. Handle 31 may be adjusted to any suitable location to effect any desired degree of opening of the valve. When valve member 26 is opened fluid may pass through passage 23 into the outlet end portion 18 of the spray nozzle.

Liquid passing through passage 23 passes through actuators or orifices 38 which are preferably at an angle of about 35° relative to the wall of cup shape member 35 and the jets which pass from orifices 38 engage vanes 45 on rotary valve member 44. The jets of liquid are effective to rotate the turbine or rotary valve member 44 at a high speed and move rotary valve plate 47 through a range of rotation which opens and closes outlet orifices 43 at a high rate of speed and permits the flow of liquid out through the orifices that are open in a pulsating strength.

The apparatus shown is designed for a relatively low volume high pressure high pulsing mode of operation. In a preferred embodiment of the apparatus, orifices 38 and 43 were 0.037" diameter and the rotary turbine or valve member 44 was about 0.80" diameter. This apparatus was effective to produce a low volume high pressure pulsating jet of liquid. At 50 psi the flow rate of liquid through spray nozzle 2 was about one-half gallon per minute or less. Rotary turbine or valve member 44 was rotated at 3600–3800 RPM under these conditions. When the liquid pressure was reduced substantially, it was possible to produce a low liquid pulse with the valve member 44 rotating at about 30 RPM and an extremely low rate of liquid flow being emitted from orifices 43 in the end of closure member 39. The apparatus, as shown, was capable of producing a steady or even operation over a very wide range of liquid pressure and liquid flow rate. As just described, the apparatus functioned smoothly at rates of rotation of valve member 44 ranging from as low as 30 RPM to as high as 3600–3800 RPM, or higher. As rotary valve member or turbine 44 rotates, the rotation of valve plate 47 opens and closes orifices 43 at a high rate of speed and permits liquid to pass out only through the orifices 43 that are open. As a result, a pulsating flow of liquid is emitted from the end of nozzle 2. The liquid that flows through the center opening 48 of rotary valve member 44 passes along the face of valve plate 47, between the valve plate and the inner surface of end wall 42 and supports valve member 44 a small predetermined distance away from end wall 42 and allows free and steady rotation of valve member 44 over a wide range of flows of liquid and a wide range of operating pressures.

While this invention has been described fully and completely with special emphasis upon a single preferred embodiment, it should be understood that within the scope of the appended claims the invention may be practiced otherwise than as specifically described herein.

I claim:

1. A pulsating spray nozzle, characterized by steady operation throughout a wide range of flow rates, comprising
   a hollow housing having fluid inlet at one end,
   an end wall closing the other end of said housing and having a plurality of fluid discharge orifices therethrough in a predetermined pattern located symmetrically around the longitudinal axis of said housing,
   a rotary valve member positioned in said housing for rotation along the surface of said end wall initially in contact therewith and movable toward and away from said surface, said valve member comprising cylindrically shaped rotary valve member having a cylindrical central passageway extending therethrough, a plurality of rotary vanes extending radially from said passageway and defining the outer boundary of said cylindrically shaped rotary member and a valve plate secured to and integral with only several of said vanes and positioned on one side of said rotary member over said several of said vanes,
   said valve member being supported for rotation in said housing with said valve plate adjacent said end wall in sliding relation therewith and over the path in which said orifices are positioned whereby rotation of said vane member closes and opens selected orifices in said end wall sequence to effect a pulsing flow of fluid therethrough without a central axle and floating longitudinally of said housing relative to said end wall,
   a second wall member in said housing between said valve member and said fluid inlet defining a chamber enclosing said valve member and having a plurality of fluid orifices extending therethrough at an angle and positioned to direct flow of fluid against said vanes to effect rotation of said vane member, and
   said valve plate having a surface adjacent said end wall having radially extending grooves therein permitting fluid flow radially outward along the surface thereof initially in contact with said end wall to support the same raised a predetermined distance from said end wall to permit steady rotation of said vane members throughout a wide range of fluid flow rate through said housing.

2. A spray nozzle according to claim 1 in which
   said housing includes a passageway interconnecting said inlet and said orifices in said second wall member, valve means supported on said housing and controlling flow of fluid through said inlet to said passageway.

3. A spray nozzle according to claim 2 in which
   said housing is of a size and shape for manual support,
   said valve means comprises a valve seat and movable valve member positioned thereagainst and urged toward closed position,
   a handle supported on the exterior of said housing, and
   means transmitting movement from said handle to said movable valve member for effecting movement thereof by operation of said handle.

4. A spray nozzle according to claim 1 in which
   said end wall comprises a cup shaped closure member threadedly secured in said other end of said housing,
   said rotary valve member being supported in the interior of said closure member for longitudinal movement and for rotation of said valve plate along the end wall thereof, and
   said valve plate being arcuate in shape and extending in an arc of less than 360° whereby fluid flow is permitted through the vanes not covered thereby.

5. A spray nozzle according to claim 4 in which
   said valve plate is arcuate in longitudinal cross-section and has said plurality of radially extending grooves in the face abutting said end wall to permit flow of fluid along said face during flow of fluid through said housing.

6. A spray nozzle according to claim 1 in which
   said other end of said housing includes a threaded recess therein,
   said second wall member being a removable wall member positioned in said recess,
   said end wall member compries a cup shaped closure member threadedly secured in said recess abutting said second wall member, and
   said rotary valve member being supported between said second wall member and said closure member for longitudinal and rotary movement therein.

7. A spray nozzle according to claim 1 in which
   said other end of said housing includes a threaded recess therein,
   said second wall member being a removable wall member positioned in said recess,
   said end wall member comprises a cup shaped closure member threadedly secured in said recess abutting said second wall member,
   said rotary valve member further comprising a semi-cylindrical core having a first plurality of vanes uniformly spaced and extending radially outward therefrom,
   said valve plate being secured on one end of said valve member and supported on the outermost two of said first plurality of vanes,
   said valve plate supporting a second plurality of vanes extending radially thereof and having a uniform spacing completing circumferentially a series of radial vanes including said first plurality of vanes, and
   said valve plate having an arcuate peripheral edge and being arcuate in longitudinal cross-section and having a plurality of radially extending grooves in the face abutting said end wall.

8. A spray nozzle according to claim 1 in which
   said valve plate is arcuate in longitudinal cross-section.

9. An irrigation lavage comprising
   a first housing having a fluid inlet and a fluid outlet,
   a thin walled flexible container for containing a medically effective liquid for cleansing wounds,
   said container having an outlet secured to said housing fluid outlet and opening into said outlet for discharging said liquid therethrough,
   said housing inlet being adapted to receive fluid under pressure into said housing to compress said flexible container to force liquid out through said outlet, and
   a fluid conduit connected at one end to said housing outlet and at the other end to the fluid inlet to a pulsating spray nozzle as defined in claim 1.

* * * * *